(12) United States Patent
Pfeiffer et al.

(10) Patent No.: US 7,666,146 B2
(45) Date of Patent: Feb. 23, 2010

(54) APPARATUS, COMPUTER SYSTEM AND COMPUTER PROGRAM FOR DETERMINING INTRATHORACIC BLOOD VOLUME AND OTHER CARDIO-VASCULAR PARAMETERS

(75) Inventors: Ulrich J. Pfeiffer, München (DE); Reinhard Knoll, München (DE); Frederic Michard, Somerville, MA (US)

(73) Assignee: Pulsion Medical Systems AG, Munich (DE)

( * ) Notice: Subject to any disclaimer, the term of this patent is extended or adjusted under 35 U.S.C. 154(b) by 979 days.

(21) Appl. No.: 11/113,407

(22) Filed: Apr. 22, 2005

(65) Prior Publication Data

US 2005/0267378 A1    Dec. 1, 2005

(30) Foreign Application Priority Data

Apr. 22, 2004    (EP) ................... 04101678

(51) Int. Cl.
*A61B 5/02* (2006.01)

(52) U.S. Cl. ............... 600/526; 600/504; 600/481

(58) Field of Classification Search ......... 600/504–507, 600/526

See application file for complete search history.

(56) References Cited

U.S. PATENT DOCUMENTS

| | | | |
|---|---|---|---|
| 5,526,817 A | 6/1996 | Pfeiffer et al. | |
| 6,394,961 B1 * | 5/2002 | Pfeiffer et al. | 600/526 |
| 6,537,230 B1 | 3/2003 | Pfeiffer et al. | |
| 6,736,782 B2 * | 5/2004 | Pfeiffer et al. | 600/481 |
| 7,209,780 B2 * | 4/2007 | Pfeiffer et al. | 600/431 |
| 2007/0282213 A1 * | 12/2007 | Michard et al. | 600/529 |

FOREIGN PATENT DOCUMENTS

| | | |
|---|---|---|
| DE | 4214402 | 11/1993 |
| DE | 10143995 | 4/2003 |
| EP | 1236435 | 9/2002 |

(Continued)

OTHER PUBLICATIONS

Godje O, Peyerl M, Seebauer T, Dewald O, and Reichert B Reproducibility of Double Indicator Dilution Measurements of Intrathoracic Blood Volume Compartments, Extravascular Lung Water, and Liver Function Chest 1998; 113; 1070-1077.*

(Continued)

*Primary Examiner*—Patricia C Mallari
*Assistant Examiner*—Karen E Toth
(74) *Attorney, Agent, or Firm*—Collard & Roe, P.C.

(57) ABSTRACT

Apparatus, computer system, computer program and storage medium for determining intrathoracic blood volume (ITBV) and other cardio-vascular parameters of a patient by thermodilution measurements. The apparatus includes: temperature influencing means for introducing a traveling temperature deviation to a patient's blood stream, a temperature sensor device for measuring the local temperature of the patient's blood downstream of the temperature influencing means, a computer system adapted to: record local blood temperature measured as a function of time to determine a thermodilution curve, determine global enddiastolic blood volume (GEDV) and intrathoracic thermovolume (ITTV) from the thermodilution curve, determine intrathoracic blood volume (ITBV) as a function of GEDV, ITTV and the airway pressure inside the patient's lungs (P). By determining ITBV not only from GEDV but also a function of ITTV and P enhanced accuracy can be obtained, especially if the patient suffers from pulmonary edema and/or is mechanically ventilated.

29 Claims, 2 Drawing Sheets

FOREIGN PATENT DOCUMENTS

| | | |
|---|---|---|
| RU | 2 179 822 CI | 2/2002 |
| WO | WO 98/21823 | 11/1993 |
| WO | WO 01/30237 | 5/2001 |

OTHER PUBLICATIONS

Godje O, Peyerl M, Seebauer T, Lamm P, Mair H, Reichart B Central venous pressure, pulmonary capillary wedge pressure and intrathoracic blood volumes as preload indicators in cardiac surgery patients European Journal of Cardio-thoracic Surgery 13 (1998) 533-540.*

Michard F, Alaya S, Zarka V, Bahloul M, Richard C, Teboul J Global End-Diastolic vol. as an Indicator of Cardiac preload in Patients With Septic Shock Chest 2003; 124; 1900-1908.*

* cited by examiner

US 7,666,146 B2

APPARATUS, COMPUTER SYSTEM AND COMPUTER PROGRAM FOR DETERMINING INTRATHORACIC BLOOD VOLUME AND OTHER CARDIO-VASCULAR PARAMETERS

CROSS REFERENCE TO RELATED APPLICATIONS

Applicant claims priority under 35 U.S.C. 119 of European Application No. 04101678.8 filed on Apr. 22, 2004.

FIELD OF THE INVENTION

The present invention relates to an apparatus, a computer system and a computer program for determining intrathoracic blood volume and other cardiovascular parameters of a patient by thermodilution measurements.

BACKGROUND OF THE INVENTION

The current state of the art in implementing transpulmonary thermodilution measurement are apparatus for injecting a bolus of thermal indicator into a patient's vena cava superior, and measuring the temperature response at a place of the patient's systemic circulation, e.g. patient's femoral artery to determine the thermodilution curve, i.e. the temperature response as a function of time. From the thermodilution curve, a schematic example of which is illustrated in FIG. 3, wherein the abscissa (time axis) 1 is linear and the ordinate (temperature difference axis) 2 is logarithmic, various cardio-vascular parameters can be derived by using computer systems running computer programs, which implement parameter calculations as disclosed in WO 93/21823, the contents of which are included herein by citation, and as set forth briefly below.

The Cardiac Output CO can be determined by algorithms based on the Stewart-Hamilton-equation:

$$CO = \frac{V_L(T_B - T_L)K_1 K_2}{\int \Delta T_B(t)\, dt}$$

where $T_B$ is the initial blood temperature, $T_L$ is the temperature of the liquid bolus, which is used as thermal indicator, $V_L$ is the thermal indicator volume, $K_1$ and $K_2$ are constants to consider the specific measurement setup, and $\Delta T_B(t)$ is the blood temperature as a function of time with respect to the baseline blood temperature $T_B$. Thermal indicator can either be colder or warmer with respect to blood temperature. To obtain cardiac output, the area under the thermodilution curve has to be determined by mathematical integration.

Other parameters that can be derived from the thermodilution curve 3 as schematically illustrated in FIG. 1 include the Exponential Decay or Downslope Time DST, i.e. the time the blood temperature difference $\Delta T_B(t)$ takes to drop by the factor $e^{-1}$, the Appearance Time AT, i.e. the time span between bolus injection IT and first appearance of a noticable temperature difference $\Delta T_B(t)$ and the Mean Transit Time MTT.

The Intrathoracic Thermovolume ITTV and the Intrathoracic blood volume ITBV can be determined as follows:

$$ITTV = CO \cdot MTT$$

$$ITBV = a' \cdot GEDV + b'$$

wherein a' and b' are species-specific constants and GEDV is the Global End-Diastolic Volume, which can be determined as follows:

$$GEDV = CO \cdot (MTT - DST)$$

An extravascular thermovolume estimate can be determined as the difference between Intrathoracic Thermovolume ITTV and the Intrathoric blood volume ITBV $$ETV = ITTV - ITBV$$

Extravascular thermovolume correlates, if there is no significant perfusion defect in the lungs (e.g. massive pulmonary embolism or large single embolism), closely to the degree of Extravascular Lung Water.

Transpulmonary thermodilution has been shown to be a reliable technique for assessing cardiac output, cardiac preload and extravascular lung water (EVLW), i.e. to quantify pulmonary edema. The estimation of EVLW by the injection of a single thermal indicator is based on the above mentioned relationship $ITBV = a' \cdot GEDV + b'$. This method has been shown to compare favorably with the double-indicator (thermo-dye) dilution technique and with the ex-vivo gravimetric methods.

However, for mechanically ventilated patients and patients suffering from severe pulmonary edema the results were not entirely satisfactory.

It is therefore an object of the present invention to provide a new apparatus, a new computer system and a new computer program allowing the determination of the intrathoracic blood volume by single indicator transpulmonary thermodilution with enhanced accuracy especially for patients suffering from severe pulmonary edema and/or for mechanically ventilated patients.

SUMMARY OF THE INVENTION

The inventors found that several factors (especially pulmonary edema and airway pressure) affect the cardiac blood/pulmonary blood volume relationship, and hence the estimation of EVLW by transpulmonary thermodilution. Indeed, edematous lung areas may compress pulmonary vessels and enhance pulmonary vasoconstriction, both factors that may reduce true pulmonary blood volume and hence lead to over-estimation of ITBV and under-estimation of extravascular lung water EVLW (when ITBV is estimated as 1.25×GEDV). Similarly, any increase in airway pressure (related either to an increase in tidal volume or the application of a positive end-expiratory pressure) may induce a decrease in pulmonary blood volume which may also change the cardiac/pulmonary blood volume ratio.

In order to accomplish the above mentioned object, the present invention provides an apparatus for determining intrathoracic blood volume (ITBV) and other cardio-vascular parameters of a patient by thermodilution measurements comprising: temperature influencing means for provoking an initial local temperature change in the proximity of a first place of a patient's vascular system, thus introducing a travelling temperature deviation to patient's blood stream, a temperature sensor device for measuring the local temperature of patient's blood at a second place of patient's vascular system downstream of said first place, a computer system connected to said temperature sensor device and adapted to record said patient's local blood temperature measured at said second place as a function of time to determine a thermodilution curve, said computer system being further adapted to determine patient's global enddiastolic blood volume (GEDV) and patient's intrathoracic thermovolume (ITTV) from said thermodilution curve said computer system being further adapted to determine patient's intrathoracic blood volume (ITBV) according to the following formula:

$$ITBV=f(GEDV,ITTV,P)$$

ITBV being the intrathoracic blood volume, GEDV being the global enddiastolic blood volume, ITTV being the intrathoracic thermovolume, P being an airway pressure inside patient's lungs.

In order to accomplish the above mentioned object, the invention also provides a computer system comprising first coupling means to couple said computer system to temperature influencing means and second coupling means to couple said computer system to a temperature sensor device and optionally third coupling means to couple said computer system to an airway pressure sensor device, and accessing means to access executable instructions to cause said computer system to control temperature influencing means for provoking an initial local temperature change in the proximity of a first place of a patient's vascular system, thus introducing a temperature deviation to patient's blood stream, to record said patient's local blood temperature measured by a temperature sensor device for measuring the local temperature of patient's blood at a second place of patient's vascular system downstream of said first place as a function of time to determine a thermodilution curve, to determine patient's global enddiastolic blood volume (GEDV) and patient's intra-thoracic thermovolume (ITTV) from said thermodilution curve, to determine patient's intra-thoracic blood volume (ITBV) according to the following formula:

$$ITBV=f(GEDV,ITTV,P),$$

ITBV being the intrathoracic blood volume, GEDV being the global enddiastolic blood volume, ITTV being the intrathoracic thermovolume, P being an airway pressure inside patient's lungs.

In order to accomplish the above mentioned object, the invention also provides a computer computer program for determining intrathoracic blood volume (ITBV) and other cardio-vascular parameters of a patient by thermodilution measurements comprising instructions executable by a computer system to cause said computer system to control temperature influencing means for provoking an initial local temperature change in the proximity of a first place of a patient's vascular system, thus introducing a temperature deviation to patient's blood stream, to record said patient's local blood temperature measured by a temperature sensor device for measuring the local temperature of patient's blood at a second place of patient's vascular system downstream of said first place as a function of time to determine a thermodilution curve, to determine patient's global enddiastolic blood volume (GEDV) and patient's intrathoracic thermovolume (ITTV) from said thermodilution curve, to determine patient's intrathoracic blood volume (ITBV) according to the following formula:

$$ITBV=f(GEDV,ITTV,P),$$

ITBV being the intrathoracic blood volume, GEDV being the global enddiastolic blood volume, ITTV being the intrathoracic thermovolume, P being an airway pressure inside patient's lungs.

By determining intrathoracic blood volume not only as a function of the global enddiastolic blood volume (GEDV) but also as a function of the intrathoracic thermovolume, experience has shown that a better estimation of intrathoracic blood volume and hence also a better estimation of extravasal lung water can be made.

According to a preferred embodiment of the invention said function f(GEDV, ITTV, P) is selected to be $$f(GEDV,ITTV,P)=a \cdot GEDV+b+c \cdot ITTV+d \cdot P$$

a being a species dependent parameter, with 1<a<2, b being a species dependent parameter, including zero, c being a species dependent parameter, with c and d being species dependent parameters, including zero, with the limitation that c and d may not be zero simultaneously.

The term c·ITTV provides for a correction especially for high values of ITTV and the term d·p provides for a correction of ITBV especially when the patient is mechanically ventilated. Once the species-specific parameters a, b, c, and d have been determined the application of this formula allows an optimal coincidence between the estimated values of intrathoracic blood volume and extravasal lung water with precisely measured values in a large population of patients.

In another preferred embodiment of the invention said function f(GEDV, ITTV, P) is selected to be $$f(GEDV, ITTV, P) = \frac{a}{c \cdot \frac{(ITTV - GEDV)}{(ITTV_{norm} - GEDV_{norm})} + d \cdot \frac{P}{P_{norm}}} GEDV + b$$

a, b, c, and d being species dependent parameters, with 1<a/(c+d)<2, wherein ITTVnorm, GEDVnorm and Pnorm are empirical normal values of ITTV, GEDV and P, respectively. Parameters a, b, c, and d are determined by regression.

In another preferred embodiment of the invention said function f(GEDV, ITTV, P) is selected to be $$ITBV = \frac{a \cdot GEDV}{\left[c2 \cdot \frac{(ITTV - GEDV)}{(ITTVnorm - GEDVnorm)} + 1\right] \cdot \left[d2 \cdot \frac{P}{Pnorm} + 1\right]} + b + c1 \cdot \frac{(ITTV - GEDV)}{(ITTVnorm - GEDVnorm)} + d1 \cdot \frac{P}{Pnorm}$$

parameters a, b, c1, d1, c2, d2 can be obtained by a nonlinear regression from comparative double dilution measurements. The parameters are species dependent. The term a/((c2+1)(d2+1)) is normally in the range of 0.5 to 10.

The first part $$ITBV = a \cdot GEDV + b + c1 \cdot \frac{(ITTV - GEDV)}{(ITTVnorm - GEDVnorm)} + d1 \cdot \frac{P}{Pnorm}$$

describes the total displacement from the thorax to the large circulation.

The second part $$ITBV = \frac{a \cdot GEDV}{\left[c2 \cdot \frac{(ITTV - GEDV)}{(ITTVnorm - GEDVnorm)} + 1\right] \cdot \left[d2 \cdot \frac{P}{Pnorm} + 1\right]} + b$$

describes the changed relation between GEDV and PBV.

Investigations have shown that with the formula according to the prior art ITBV i.e. the sum of PBV and GEDV was underestimated at high ETV and at high airway pressures. This is because a high ETV leads to a tension of the lung tissue, which is disturbing the normal fixed relation between PBV and GEDV (ITBV=GEDV+PBV=a*GEDV+b). A similar result is reached at high airway pressure P.

Thereby the effective pressure, which is pushing blood out of the lung, is the transmural pressure Ptm=ITP−Pmv. This is the difference between intra thoracic pressure and micro vascular pressure. The peri micro vascular pressure could be neglected. If the lung is very stiff e.g. at a fibrosis, even a high airway pressure has little influence—the intra thoracic pressure remains low.

Mostly Ptm in the micro vessels of the lung is not available. In this case the intra thoracic pressure or the mean airway pressure could be used instead. Because PEEP (positive end expiratory Pressure) is correlated, it could be also useful.

The blood is displaced from the lung in two ways
1. a fraction of the blood is shifted from the lungs into the heart, thereby the normal relation between GEDV and PBV is changed
2. a part of the PBV is totally displaced from the thorax to the large circulation (systemic circulation)

Dependent on the dominant factor $c_1$, $d_1$ or $c_2$, $d_2$ could be equal to zero. In a special case of humans a=1.48; b=87 ml; $c_1$=−0.18; $d_1$=0; $c_2$=0; $d_2$=0

There are also other formulas possible. In general ITBV is a function of GEDV, ITTV and P. It could also be advantageous to apply this to intra thoracic blood volume Index ITBVI=ITBV/BSA which is the ITBV divided by Body surface Area (BSA). In this case ITBVI is a function of GEDV/BSA, TTV/BSA and P.

In another preferred embodiment of the invention P is set equal to a transmural lung pressure Ptm, being defined as Ptm=ITP−Pmv, ITP being a intrathoracic pressure and Pmv being a microvascular pressure. As it is the transmural pressure which is responsible for pulmonary vasoconstriction and which is the reason for an overestimation of the intrathoracic blood volume and the underestimation of extravascular lung water best results are obtained by using the transmural pressure for correction of the intrathoracic blood volume, even if the patient suffers from lung fibrosis.

However, the transmural pressure is sometimes difficult to determine. Fairly good results are also obtained according to another embodiment by using for P a mean pressure measured in the airway of a mechanical respirator or a positive end expiratory pressure (PEEP) of a mechanical respirator. These pressures can be determined easily.

Further advantageous embodiments are described in the subclaims.

The accompanying drawings serve for a better understanding of the above and other features of the present invention.

DETAILED DESCRIPTION

Figure 1:
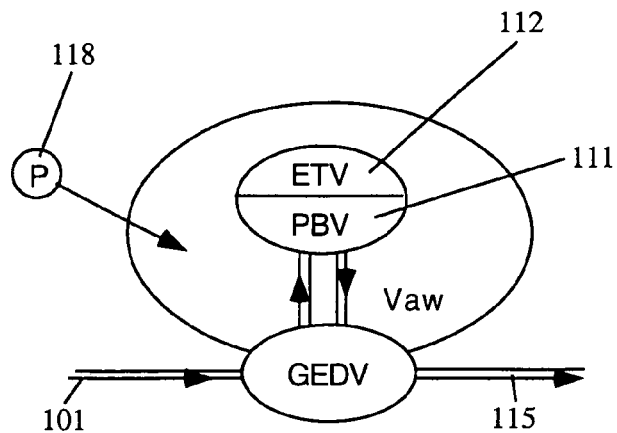
FIG. 1 shows a schematic illustration explaining the dependencies between global end diastolic volume GEDV, pulmonal blood volume PBV, extra thermal volume ETV, airway volume Vaw, and airway pressure P.

FIG. 1 shows a schematic illustration explaining the dependencies between global end diastolic volume GEDV, which is roughly the blood located in the heart, pulmonal blood volume PBV 111, which is the blood located in the lungs, extra thermal volume ETV 112, which is roughly the lung water outside the vessels, air way volume Vaw, and air way pressure P. Increasing airway pressure P causes the air way volume Vaw to increase, which leads to a decrease of pulmonal blood volume PBV, in other words, the increasing P causes blood to flow out from the lungs into the heart and/or into the systemic circulation. Similarly, increasing ETV also causes blood to flow out from the lungs into the heart and/or into the systemic circulation.

Figure 2:
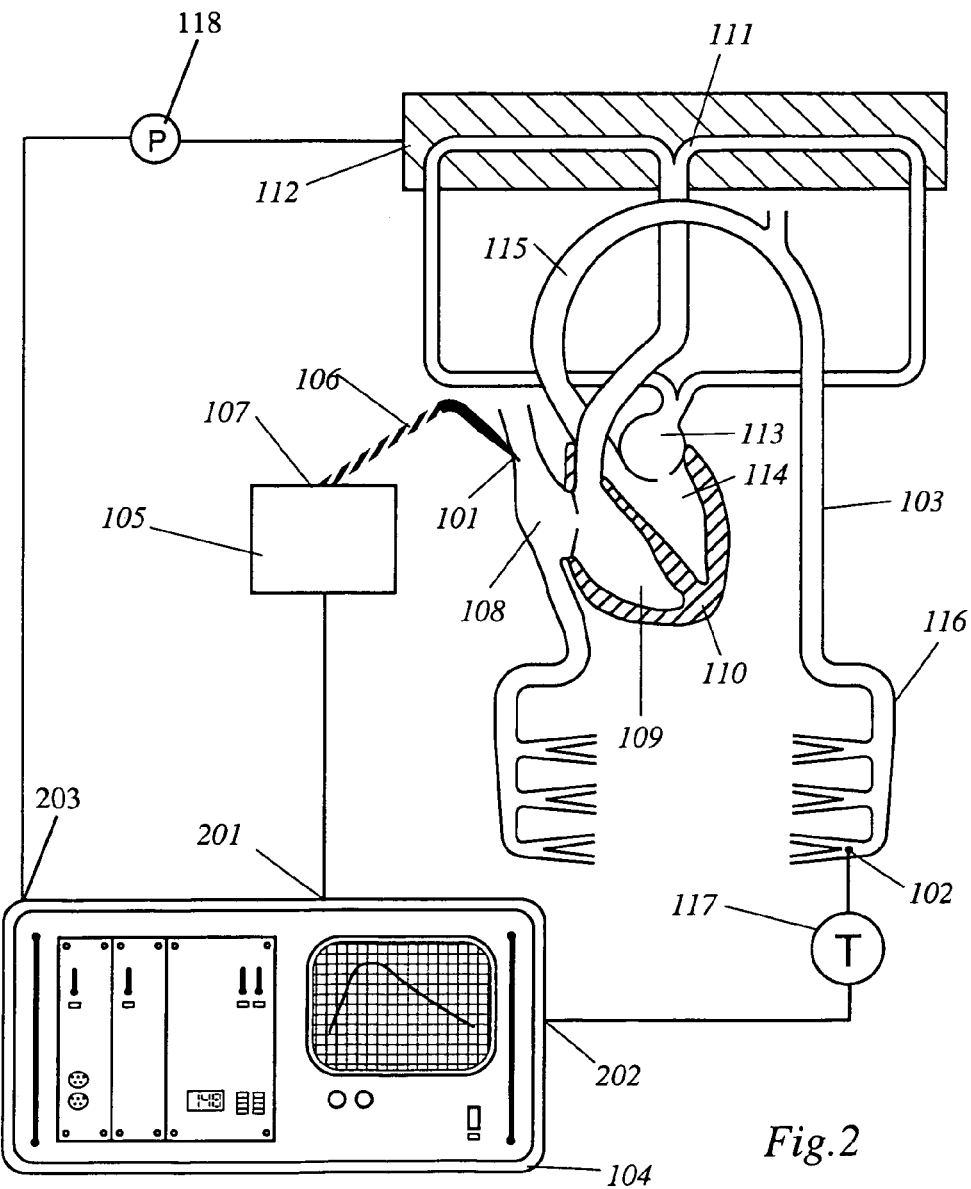
FIG. 2 shows a schematic sketch of both a patient's vascular system and a preferred embodiment of an apparatus according to the present invention.
Figure 3:
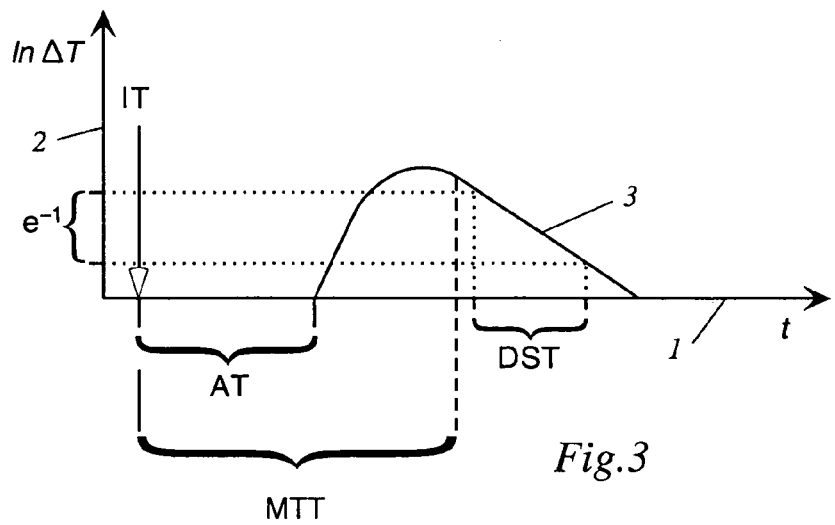
FIG. 3 shows a schematic example of a Thermodilution Curve in a diagram with the blood temperature difference as a function of time, wherein the abscissa is linear and the ordinate is logarithmic.
Figure 4:
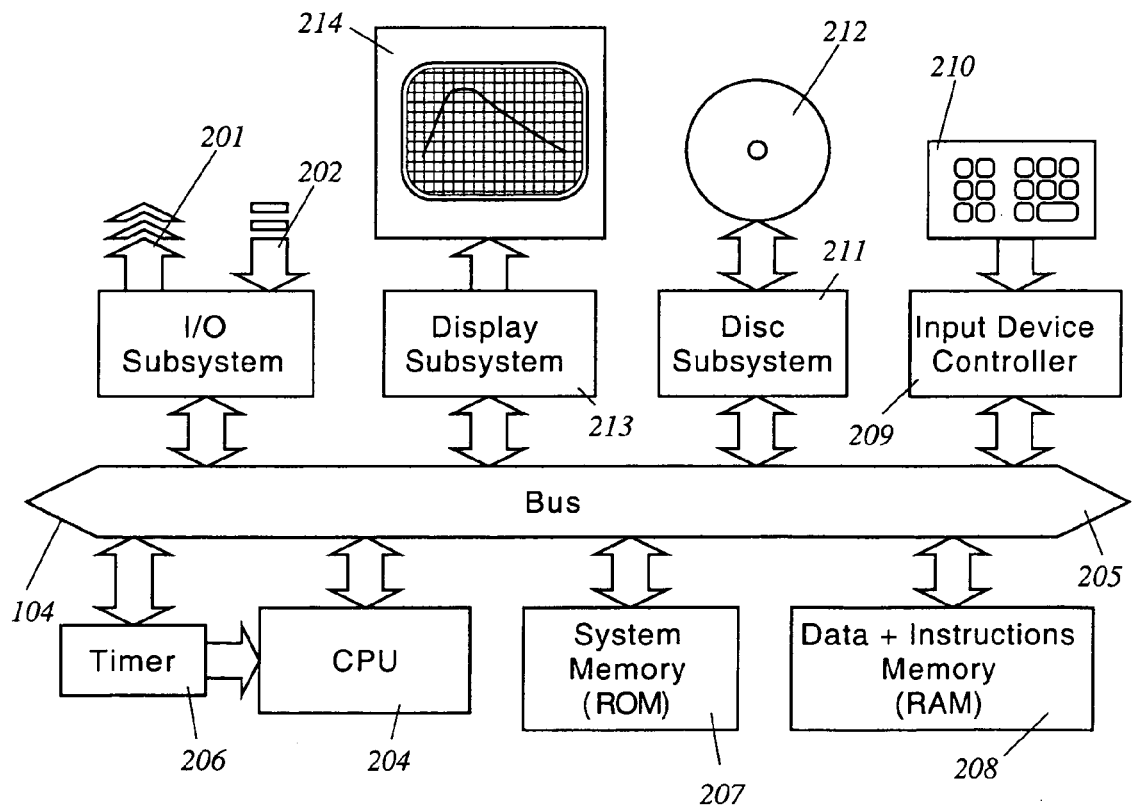
FIG. 4 shows a block diagram illustrating the general hardware structure of an embodiment of a computer system according to the present invention being part of the apparatus sketched in FIG. 2.

FIG. 2 illustrates the main components necessary to implement an embodiment of an apparatus according to the invention and schematically shows the first and second places 101, 102 of a patient's vascular system 103, where the apparatus interacts with the patient's vascular system 103. A computer system 104, the general hardware structure of which is schematically illustrated in FIG. 4, is connected via port A 201 with a medical dosage device 105 serving together with a catheter 106 as an injection means 107 to inject at the first place 101, e.g. into patient's vena cava superior, a bolus, e.g. 10 ml, or, as a guideline, 0.15 ml/kg patient's body mass. The bolus serving as a thermal indicator liquid is substantially warmer or colder than patient's blood temperature. As a result, travelling temperature deviation is introduced to the patient's vascular system 103, where it continuously changes according to boundary conditions. The temperature deviation passes right atrium and right ventricle 109 of patient's heart 110 to enter the pulmonary circulation 111, where an extravascular thermovolume 112 may be present in the proximity of the patient's vessels. The temperature deviation passes the left atrium 113 and the left ventricle 114 of patient's heart to enter through the aorta 115 the systemic circulation 116. When the travelling temperature deviation reaches the second place 102, e.g. patient's arteria femoralis, where the patient's blood temperature is continuously measured by a sensor device 117, which is connected to the computer system 104 via port B 202, the travelling temperature deviation is recorded by the computer system 104 as Thermodilution Curve, i.e. temperature measured at the second place 102 as function of time. From this Thermodilution Curve the computer system 104 determines an extravascular thermovolume estimate according to the relations explained above. Extravascular thermovolume correlates, if there is no significant perfusion defect in the lungs (e.g. pulmonary embolism), closely to the degree of Extravascular Lung Water.

FIG. 4 illustrates the general hardware structure of an embodiment of a computer system 104 according to the invention; suitable to be part of the apparatus shown in FIG. 2. Via ports A and B 201, 202 which belong to an input/output subsystem, the computer system 104 is connectable to injection means 107 sensor device 117 and pressure sensor 118, respectively. The input/output subsystem is controlled by a central processing unit (CPU) 204, which communicates via a data and adress bus 205 with the other components of the computer system 104, which include a timer 206 providing timer clock signals to the CPU 204, a system memory (ROM)

207, in which the system software is permanently stored, a data and instructions memory (RAM) 208, where both executable instructions and various data including temperature readings for thermodilution curves and airway pressure readings can be stored, an input device controller 209 controlling an input device 210, such as a keypad, a touch screen or the like, for manually entering system parameters, operation settings and the like, a disc subsystem 211 to read data or program instructions from a storage medium 212, such as a hard disc, floppy disc, compact disc, optical disc or the like, and to store data to the storage medium 212, and a display subsystem 213 controlling a display 214 to display relevant information, such as a Thermodilution Curve or cardiovascular parameters determined by the computer system 104. The pressure sensor device 118, which is adapted to measure the pressure in patient's airway is connected to the computer system 104 via port 203.

The above described apparatus is adapted to determine MTT, DST, CO from the thermodilution curve and to calculate parameters such as GEDV, ITBV and ETV.

The invention claimed is:

1. An apparatus for determining intrathoracic blood volume (ITBV) and other cardio-vascular parameters of a patient by thermodilution measurements comprising:
   a) temperature influencing means for provoking an initial local temperature change in the proximity of a first place of a patient's vascular system, thus introducing a traveling temperature deviation to patient's blood stream,
   b) a temperature sensor device for measuring the local temperature of patient's blood at a second place of patient's vascular system downstream of said first place,
   c) means for determining a pressure at least approximately representing an airway pressure of said patient,
   d) a computer system coupled to said temperature sensor device and said means for determining said pressure and adapted to record said patient's local blood temperature measured at said second place as a function of time to determine a thermodilution curve,
   e) said computer system being further adapted to determine patient's global enddiastolic blood volume (GEDV) and patient's intrathoracic thermovolume (ITTV) from said thermodilution curve,
   f) said computer system being further adapted to determine patient's intrathoracic blood volume (ITBV) according to the following formula:

$ITBV = f(GEDV, ITTV, P)$,

ITBV being the intrathoracic blood volume, GEDV being the global enddiastolic blood volume, ITTV being the intrathoracic thermovolume, P being said airway pressure inside patient's lungs.

2. The apparatus according to claim 1, wherein said function f(GEDV, ITTV, P) is selected to be $f(GEDV, ITTV, P) = a \cdot GEDV + b \cdot ITTV + d \cdot P$ a being a species dependent parameter, with $1 < a < 2$
   b being a species dependent parameter, including zero
   c being a species dependent parameter, with $c \leq 0$
   d being a species dependent parameter, including zero, with the restriction that c and d may not be zero simultaneously.

3. The apparatus according to claim 1, wherein said function f(GEDV, ITTV, P) is selected to be $$f(GEDV, ITTV, P) = \frac{a}{c\frac{(ITTV - GEDV)}{(ITTV_{norm} - GEDV_{norm})} + d\frac{P}{P_{norm}}} GEDV + b$$

a, b, c, and d being species dependent parameters, with $1 < a/(c+d) < 2$, wherein ITTVnorm, GEDVnorm and Pnorm are empirical normal values of ITTV, GEDV and P, respectively.

4. The apparatus according to claim 1, wherein said function f(GEDV, ITTV, P) is selected to be $$ITBV = \frac{a \cdot GEDV}{\left[c2 \cdot \frac{(ITTV - GEDV)}{(ITTVnorm - GEDVnorm)} + 1\right] \cdot \left[d2 \cdot \frac{P}{Pnorm} + 1\right]} + b + c1 \cdot \frac{(ITTV - GEDV)}{(ITTVnorm - GEDVnorm)} + d1 \cdot \frac{P}{Pnorm}$$

a, b, c1, c2, d1, d2 being species dependent parameters, with $0.5 \leq a/(c2+1)(d2+1) \leq 10$, wherein ITTVnorm, GEDVnorm and Pnorm are empirical normal values of ITTV, GEDV and P, respectively.

5. The apparatus according to claim 1 wherein P is set equal to a transmural lung pressure Ptm, being defined as $Ptm = ITP - Pmv$, ITP being a intrathoracic pressure and Pmv being a microvascular pressure.

6. The apparatus according to claim 1, wherein P is a pressure measured in the airway of a mechanical respirator.

7. The apparatus according to claim 6, wherein P is a positive end expiratory pressure (PEEP).

8. The apparatus according to claim 1, wherein P is a mean airway pressure.

9. The apparatus according to claim 1 which is adapted to determine at least one of said cardio-vascular parameters by transpulmonary thermodilution.

10. The apparatus according to claim 1 which is adapted to determine an estimate of extravascular lung water (EVLW) as $EVLW = ITTV - ITBV$, EVLW being the extravascular lung water.

11. The apparatus according to claim 1 which is adapted to determine ITTV as $ITTV = CO \cdot MTT$, CO being the cardiac output and MTT being the mean transit time, indicating the time required by said temperature deviation to travel from said first place to said second place.

12. The apparatus according to claim 1 which is adapted to determine GEDV as $GEDV = CO \cdot (MTT - DST)$, CO being the cardiac output and MTT being the mean transit time, indicating the time required by said temperature deviation to travel from said first place to said second place and DST being a down slope time of said thermodilution curve.

13. The apparatus according to claim 1 further comprising a pressure sensing device coupled to said computer system.

14. A computer system comprising first coupling means to couple said computer system to temperature influencing means, second coupling means to couple said computer system to a temperature sensor device, third coupling means for coupling said computer system to means for determining a pressure at least approximately representing an airway pressure of said patient, and accessing means to access executable instructions to cause said computer system
- a) to control temperature influencing means for provoking an initial local temperature change in the proximity of a first place of a patient's vascular system, thus introducing a traveling temperature deviation to patient's blood stream,
- b) to record said patient's local blood temperature measured by a temperature sensor device for measuring the local temperature of patient's blood at a second place of patient's vascular system downstream of said first place as a function of time to determine a thermodilution curve,
- c) to determine patient's global enddiastolic blood volume (GEDV) and patient's intrathoracic thermovolume (ITTV) from said thermodilution curve,
- d) to determine patient's intrathoracic blood volume (ITBV) according to the following formula:

$$ITBV = f(GEDV, ITTV, P),$$

ITBV being the intrathoracic blood volume, GEDV being the global enddiastolic blood volume, ITTV being the intrathoracic thermovolume, P being said airway pressure inside patient's lungs.

15. The computer system according to claim 14, wherein said function f(GEDV, ITTV, P) is selected to be $$f(GEDV, ITTV, P) = a \cdot GEDV + b + c \cdot ITTV + d \cdot P$$

a being a species dependent parameter, with $1 < a < 2$
b being a species dependent parameter, including zero
c being a species dependent parameter, with $c \leq 0$
d being a species dependent parameter, including zero, with the restriction that c and d may not be zero simultaneously.

16. The computer system according to claim 14, said function f(GEDV, ITTV, P) is selected to be $$f(GEDV, ITTV, P) = \frac{a}{c \frac{(ITTV - GEDV)}{(ITTV_{norm} - GEDV_{norm})} + d \frac{P}{P_{norm}}} GEDV + b$$

a, b, c, and d being species dependent parameters, with $1 < a/(c+d) < 2$, wherein $ITTV_{norm}$, $GEDV_{norm}$ and $P_{norm}$ are empirical normal values of ITTV, GEDV and P, respectively.

17. The computer system according to claim 14, wherein said function f(GEDV, ITTV, P) is selected to be $$ITBV = \frac{a \cdot GEDV}{\left[c2 \cdot \frac{(ITTV - GEDV)}{(ITTVnorm - GEDVnorm)} + 1\right] \cdot \left[d2 \cdot \frac{P}{Pnorm} + 1\right]} + b + c1 \cdot \frac{(ITTV - GEDV)}{(ITTVnorm - GEDVnorm)} + d1 \cdot \frac{P}{Pnorm}$$

a, b, c1, c2, d1, d2 being species dependent parameters, with $0.5 \leq a/(c2+1)(d2+1) \leq 10$, wherein $ITTVnorm$, $GEDVnorm$ and $Pnorm$ are empirical normal values of ITTV, GEDV and P, respectively.

18. The computer system according to claim 14, comprising a port coupled to a pressure sensor arranged in the airway of a mechanical respirator.

19. The computer system according to claim 14 being caused to determine an estimate of extravascular lung water (EVLW) as $$EVLW = ITTV - ITBV,$$

EVLW being the extravascular lung water.

20. The computer system according to claim 14 being caused to determine said ITTV as $$ITTV = CO \cdot MTT,$$

CO being the cardiac output and MTT being the mean transit time, indicating the time required by said temperature deviation to travel from said first place to said second place.

21. The computer system according to claim 14 being caused to determine said GEDV as $$GEDV = CO \cdot (MTT - DST),$$

CO being the cardiac output and MTT being the mean transit time, indicating the time required by said temperature deviation to travel from said first place to said second place and DST being a down slope time of said thermodilution curve.

22. A computer program for determining intrathoracic blood volume (ITBV) and other cardio-vascular parameters of a patient by thermodilution measurements comprising instructions executable by a computer system to cause said computer system
- a) to control temperature influencing means for provoking an initial local temperature change in the proximity of a first place of a patient's vascular system, thus introducing a travelling temperature deviation to patient's blood stream,
- b) to record said patient's local blood temperature measured by a temperature sensor device for measuring the local temperature of patient's blood at a second place of patient's vascular system downstream of said first place (101) as a function of time to determine a thermodilution curve,
- c) to read in a pressure at least approximately representing an airway pressure of said patient,
- d) to determine patient's global enddiastolic blood volume (GEDV) and patient's intrathoracic thermovolume (ITTV) from said thermodilution curve,
- e) to determine patient's intrathoracic blood volume (ITBV) according to the following formula:

$$ITBV = f(GEDV, ITTV, P),$$

ITBV being the intrathoracic blood volume, GEDV being the global enddiastolic blood volume, ITTV being the intrathoracic thermovolume, P being an airway pressure inside patient's lungs.

23. The computer program according to claim 22, wherein said function f(GEDV, ITTV, P) is selected to be $$f(GEDV, ITTV, P) = a \cdot GEDV + b + c \cdot ITTV + d \cdot P$$

a being a species dependent parameter, with $1 < a < 2$
b being a species dependent parameter, including zero
c being a species dependent parameter, with $c \leq 0$
d being a species dependent parameter, including zero, with the restriction that c and d may not be zero simultaneously.

24. The computer program according to claim 22, said function f(GEDV, ITTV, P) is selected to be $$f(GEDV, ITTV, P) = \frac{a}{c\frac{(ITTV-GEDV)}{(ITTV_{norm}-GEDV_{norm})} + d\frac{P}{P_{norm}}} GEDV + b$$

a, b, c, and d being species dependent parameters, with $1 < a/(c+d) < 2$, wherein ITTVnorm, GEDVnorm and Pnorm are empirical normal values of ITTV, GEDV and P, respectively.

25. The computer program according to claim 22, wherein said function f(GEDV, ITTV, P) is selected to be $$ITBV = \frac{a \cdot GEDV}{\left[c2 \cdot \frac{(ITTV-GEDV)}{(ITTVnorm-GEDVnorm)} + 1\right] \cdot \left[d2 \cdot \frac{P}{Pnorm} + 1\right]} + b + c1 \cdot \frac{(ITTV-GEDV)}{(ITTVnorm-GEDVnorm)} + d1 \cdot \frac{P}{Pnorm}$$

a, b, c1, c2, d1, d2 being species dependent parameters, with $0.5 \leq a/(c2+1)(d2+1) \leq 10$, wherein ITTVnorm, GEDVnorm and Pnorm are empirical normal values of ITTV, GEDV and P, respectively.

26. The computer program according to claim 22 causing said computer system to determine an estimate of extravascular lung water (EVLW) as

*EVLW=ITTV−ITBV,*

EVLW being the extravascular lung water.

27. The computer program according to claim 22 causing said computer system to determine ITTV as

*ITTV=CO·MTT,*

CO being the cardiac output and MTT being the mean transit time, indicating the time required by said temperature deviation to travel from said first place to said second place.

28. The computer program according to claim 22 causing said computer system to determine GEDV as

*GEDV=CO·(MTT−DST),*

CO being the cardiac output and MTT being the mean transit time, indicating the time required by said temperature deviation to travel from said first place to said second place and DST being a down slope time of said thermodilution curve.

29. A storage medium having physically stored thereon a computer program as claimed in claim 22.

* * * * *

UNITED STATES PATENT AND TRADEMARK OFFICE
CERTIFICATE OF CORRECTION

PATENT NO. : 7,666,146 B2 Page 1 of 1
APPLICATION NO. : 11/113407
DATED : February 23, 2010
INVENTOR(S) : Pfeiffer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1293 days.

Signed and Sealed this

Seventh Day of December, 2010

David J. Kappos
*Director of the United States Patent and Trademark Office*